(12) United States Patent
Studer

(10) Patent No.: US 7,430,946 B2
(45) Date of Patent: Oct. 7, 2008

(54) ULTRAMICROTOME DEVICE

(75) Inventor: Daniel Studer, Dotzigen (CH)

(73) Assignee: Anton Meyer & Co. AG, Nidau (CH)

( * ) Notice: Subject to any disclaimer, the term of this patent is extended or adjusted under 35 U.S.C. 154(b) by 150 days.

(21) Appl. No.: 11/497,488

(22) Filed: Aug. 1, 2006

(65) Prior Publication Data

US 2006/0266177 A1 Nov. 30, 2006

Related U.S. Application Data

(63) Continuation of application No. 10/646,354, filed on Aug. 22, 2003, now abandoned, which is a continuation-in-part of application No. 09/718,636, filed on Nov. 22, 2000, now abandoned, which is a continuation-in-part of application No. 09/207,284, filed on Dec. 8, 1998, now abandoned.

(30) Foreign Application Priority Data

Dec. 19, 1997 (EP) ................. 97 811 004

(51) Int. Cl.
*B26D 5/00* (2006.01)
(52) U.S. Cl. .............. 83/42; 83/713; 83/915.5
(58) Field of Classification Search ........ 83/42, 83/707, 713, 915.5, 956
See application file for complete search history.

(56) References Cited

U.S. PATENT DOCUMENTS

| | | |
|---|---|---|
| 3,076,904 A | 2/1963 | Kleesattel et al. |
| 3,440,913 A | 4/1969 | Persidsky et al. |
| 3,526,219 A | 9/1970 | Balamuth |
| 3,785,234 A * | 1/1974 | Sitte ................ 83/414 |
| 4,188,952 A | 2/1980 | Loschilov et al. |
| 4,377,958 A | 3/1983 | Leighton |
| 4,697,489 A | 10/1987 | Kim |
| 5,282,404 A | 2/1994 | Leighton et al. |
| 5,551,326 A | 9/1996 | Goodman |
| 5,768,970 A | 6/1998 | Wolf et al. |
| 5,935,143 A | 8/1999 | Hood |
| 6,000,309 A | 12/1999 | Gnägi |

(Continued)

FOREIGN PATENT DOCUMENTS

BE 440928 A 3/1941

(Continued)

OTHER PUBLICATIONS

Patent Abstract of Japan, vol. 006, No. 188 (p. 144), Sep. 28, 1982 & JP 57 100335 A (Tamura Isamu, Jun. 22, 1982).

(Continued)

*Primary Examiner*—Kenneth E. Peterson
(74) *Attorney, Agent, or Firm*—The Webb Law Firm

(57) ABSTRACT

In a process for cutting sections from a probe for microscopic analysis, an ultramicrotome device is used having a blade with a cutting edge, the cutting edge extending at least approximately in a first direction. The process includes the steps of: vibrating the blade in the first direction; and moving the blade relative to the probe to be cut in a second direction, the second direction being perpendicular to the first direction. This eliminates, or at least strongly reduces, compression of the cut sections.

13 Claims, 4 Drawing Sheets

U.S. PATENT DOCUMENTS 6,041,686 A    3/2000   Lihl et al.

FOREIGN PATENT DOCUMENTS

| DE | 913 112 C   | 9/1950 |
|----|-------------|--------|
| DE | 1 267 873   | 5/1968 |
| DE | 1561 99 A   | 8/1982 |
| DE | 38 20 085 C1| 7/1989 |
| DE | 3 902 109   | 7/1990 |
| JP | 3581153431 A| 7/1983 |

OTHER PUBLICATIONS

D. Studer and H. Gnaegi, "Minimal compression of ultrathin sections with use of an oscillating diamond knife", *Journal of Microscopy*, vol. 197, Pt. 1. Jan. 2000, pp. 94-100 (USA).

* cited by examiner

ULTRAMICROTOME DEVICE

CROSS REFERENCE TO RELATED APPLICATIONS

This application is a continuation of U.S. patent application Ser. No. 10/646,354, filed Aug. 22, 2003, now abandoned which is a continuation-in-part of U.S. patent application Ser. No. 09/718,636, filed Nov. 22, 2000, now abandoned which is a continuation-in-part of U.S. patent application Ser. No. 09/207,284, filed Dec. 8, 1998, now abandoned which claims priority to European Patent No. EP 97 811 004.7, filed Dec. 19, 1997, all of which are incorporated herein by reference in their entirety.

BACKGROUND OF THE INVENTION

1. Field of the Invention

The present invention relates to a process for cutting sections from a probe for microscopic analysis by using an ultramicrotome device.

2. Description of Related Art

Microtomes and ultramicrotomes are used to cut thin respective ultra-thin sections from a sample for microscopic analyses. The sample is mounted on a cross-slide which can be advanced horizontally in steps according to the desired thickness of the sections and vertically for performing the cutting operation. A cutting blade with a horizontal cutting edge is mounted on a holder. Microtomy is concerned with a range of thickness of 0.5 to 50 μm of the sections and is mainly used for optical microscopy. Ultramicrotomy is concerned with a range of thickness of 10 to 100 nm of the sections. This range of thickness is required for transmission electron microscopy. Ultramicrotomy has proved to be a very fast and efficient technique not only for TEM but also for surfacing samples for STM and AFM.

In microtomy mainly steel blades are used for cutting. German Patent No. 913 112 discloses an older type of a microtome in which the cutting blade is horizontal and the sample advances upwardly in steps between the cuts. The blade is fastened between two parallel leaf springs and driven by magnets for oscillating movement parallel to the cutting edge. The cutting edge of a steel blade is relatively rough when viewed under an electron microscope and relatively blunt. With the oscillating motion of the blade, therefore, a sawing action is achieved: the jags of the cutting edge act like saw teeth.

This sawing action of the blade in a microtome is also described in the DDR Patent No. 156 199, in which the blade is driven by an electroacoustical transducer at high frequency, and in the Belgian Patent No. 440 928 which uses an ultrasound emitter to oscillate the blade.

In ultramicrotomy the sections are so thin that extreme care must be taken to shield the ultramicrotome from all possible external and internal vibrations because they would adversely affect the cutting result. It therefore seemed impossible to transfer the sawing action of the cutting blade known from microtomy to an ultramicrotome. For this reason much sharper and perfectly rectilinear cutting edges are required in ultramicrotomy. This has been achieved by cutting blades of diamond. U.S. Pat. No. 4,697,489 describes a holder with such a diamond cutting blade for ultramicrotomes. With the perfectly rectilinear cutting edge, even when viewed under an electron microscope, of a diamond blade no sawing action can be achieved as with steel blades.

For the ultramicrotomy at room temperature, usually the cutting is performed on a knife mounted in a boat which contains water. The water forms a horizontal surface behind the cutting edge of the knife. Due to the surface tension the sections float on the water surface and can be collected. The water acts as a lubricant during sectioning process.

However, in ultramicrotomy a different problem arises which does not occur in microtomy: the problem of section compression. This phenomenon occurs at a thickness of the sections below 100 nm. Depending on the mechanical properties of the sample (flexibility) and on the sectioning angle $\phi$ of the knife the sections undergo considerable distortion (compression) during cutting (FIG. 8). In FIG. 8, 1 designates the diamond blade or knife with the cutting edge 2. 3 is the sample. The sample 3 may be one of a great variety of industrial or biological samples. A is the vertical movement of the sample 3. 4 is the cut section floating on a waterbed 5. 6 designates the direction of compression in the section 4. 7 is a region of intense shearing, and 8 is the region of compression in the sample 3.

Water sensitive samples 3 have to be cut dry. Due to the missing lubrication and to the friction on the knife surface the sections 4 are even more compressed as the ones cut on water. In cryo-UM most samples have to be cut dry. The amount of compression depends on different factors:

The sectioning angle of the knife.

The hardness of the sample.

The triboelectrical properties of the sample.

The most critical factor is the sectioning angle $\phi$. The sectioning angle $\phi$ is the sum of the wedge angle $\beta$ of the knife 1 and the clearance angle $\delta$. It was shown that reducing the wedge angle $\beta$ results in a reduction of compression. However, the wedge angle $\beta$ may not be reduced ad infinitum. We have found an angle of 30° to be a limit. A further reduction of the wedge angle results in a lower cutting edge 2 quality and in a considerably shorter service time of the knife 1. In cryo-UM the compression in sections was found almost equal with the sectioning angle $\phi$. Therefore, a knife 1 working with a sectioning angle $\phi$ of 40° (wedge angle $\beta$ 30°, clearance angle $\delta$ 10°) would result in a compression in the sections 4 of approximately 40%.

SUMMARY OF THE INVENTION

In order to preserve the original ultrastructure and form of matter, it would be desirable to eliminate the distortion (compression) in the sections 4.

The problem to be solved with the present invention is to create a process used in an ultramicrotome which reduces or eliminates the compression of the sections. This problem is solved by the present inventive process for cutting sections from a probe for microscopic analysis, by using an ultramicrotome device having a blade, especially a diamond blade, with a cutting edge, wherein this cutting edge extends in a non-vibrated position at least approximately in a first direction. This process comprises the steps of vibrating said blade in the first direction and moving the blade relative to the probe to be cut in a second direction, the second direction being perpendicular to the first direction.

Briefly stated, the device used in such a process comprises a holder and a block attached to the holder by at least one spring. A diamond blade is attached to the block. The cutting edge of the blade is substantially horizontal in operation. A vibrator cooperates with the block to vibrate it substantially parallel to the cutting edge. Preferably, the vibrator comprises a piezoelectric transducer.

DETAILED DESCRIPTION OF PREFERRED EMBODIMENTS

Figure 1:
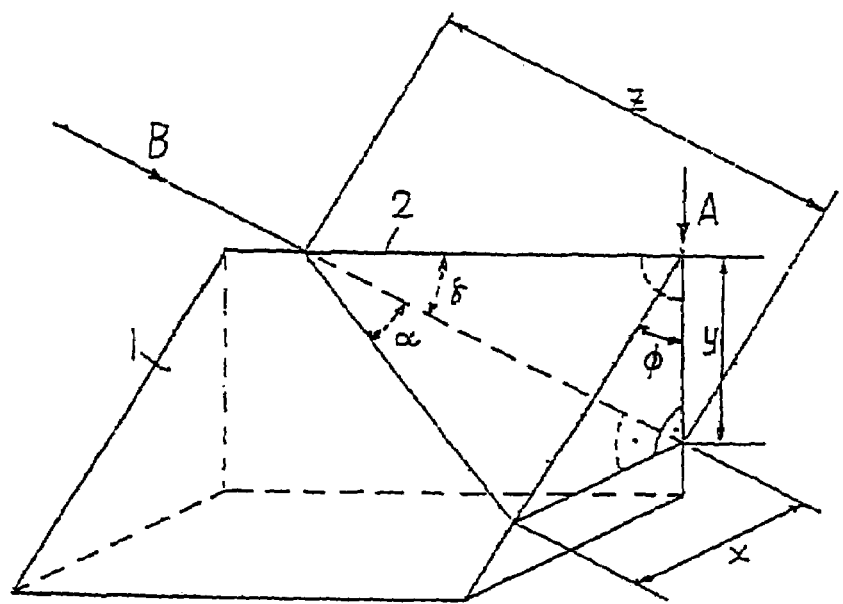
FIG. 1 is a schematic diagram showing the effective sectioning angle α when the blade or knife 1 is moved in the direction of the edge 2 during cutting.

In the present invention an oscillating movement of the blade or knife 1 parallel to the cutting edge 2 and perpendicular to the cutting direction A is used to eliminate or at least strongly reduce compression of the sections 4. When the knife 1 moves in the direction of the cutting edge 2 while the probe 3 moves in the direction A, an effective cutting direction B results which forms an acute angle γ with the cutting edge 2 (FIG. 1). If y is the vertical movement of the probe 3 per time unit and z is the effective relative movement between knife 1 and probe 3 in the same time unit, it can be seen from FIG. 1 that $$\tan\alpha = \frac{x}{z};$$
$$\sin\gamma = \frac{y}{z};$$
$$\tan\phi = \frac{x}{y}.$$

It follows:

$$\sin\gamma \cdot \tan\phi = \frac{y}{z} \cdot \frac{x}{y} = \frac{x}{z} = \tan\alpha.$$

When the knife 1 vibrates, the effective sectioning angle α varies (maximum effective sectioning angle α equal to φ, minimal effective sectioning angle α close to 0°). The theoretical value of compression reduction is as follows: An assumed mean effective sectioning angle α depends on the amplitude C (mm) and the frequency ν (Hz) of the vibration and on the cutting speed v (mm/sec). Only small effective sectioning angles α are considered. Under this assumption it can be shown that $$\tan\alpha = (v/C\cdot\nu)\tan\phi.$$

To give an example, the following parameters are assumed:

φ=45°; v=0.1 mm/sec; C=1 μm; ν=1 kHz.

It follows tan α=(0.1 mm/sec)/(0.001 mm·1000 Hz)·1=0.1 resulting in a mean effective sectioning angle α of about 5.7°.

The theoretical assumptions seem to be correct because on a prototype the oscillating knife has shown to significantly reduce the compression of the sections 4.

In ultramicrotomy the persons skilled in the art have taken extreme care to shield the microtome from all possible external and internal vibrations because they adversely affect the cutting result. The inventor has overcome this prejudice and could show that by vibrating the knife 1 substantially parallel to the cutting edge 2, no adverse effect of the vibration was observed.

Figure 2:
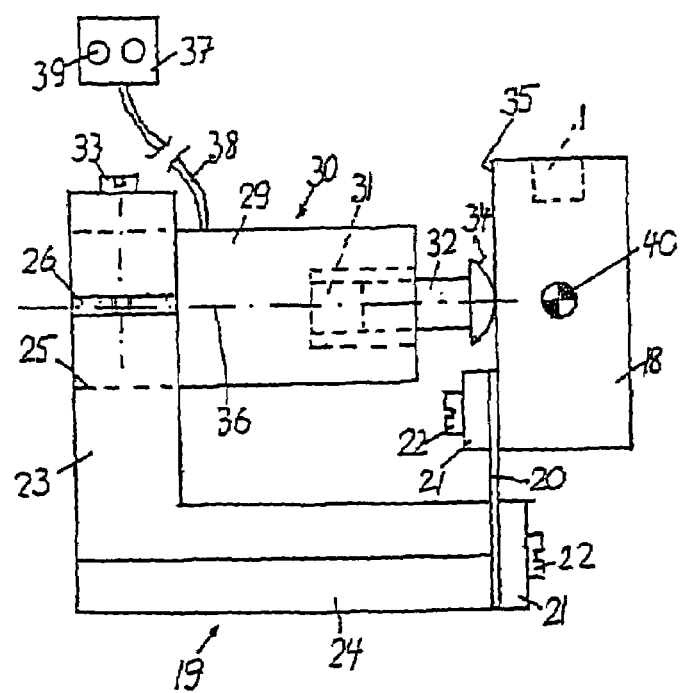
FIG. 2 is a side view of a first embodiment according to the present invention.
Figure 3:
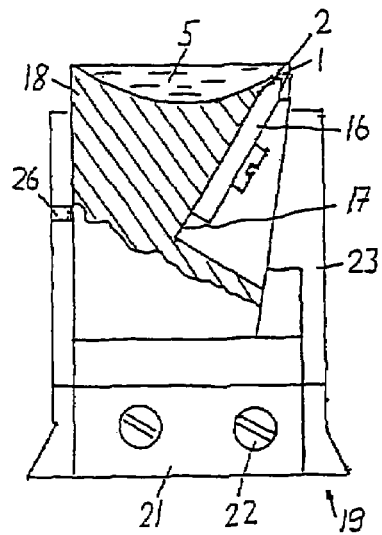
FIG. 3 is a front view, partially in section, of the first embodiment of FIG. 2.

A first embodiment of the invention is shown in FIGS. 2 and 3. The blade 1 is sintered in a bronze holder 16 or vacuum brazed in a tungsten carbide holder. The holder 16 is mounted on an inclined face of a recess 17 in a block 18. The block 18 is mounted to a holder 19 by means of a leaf spring 20. The plane of the leaf spring 20 is substantially vertical and perpendicular to the cutting edge 2. The spring 20 is mounted to the block 18 and the holder 19 by flat plates 21 and screws 22. Alternatively, the spring 20 may be designed as an integral part of the block 18 and the holder 19.

An arm 23 extends upward from the base 24 of the holder 19. The arm 23 has a cylindrical horizontal boring 25 and a slot 26 on one side. The cylindrical housing 29 of a vibrator 30 with a piezoelectric transducer 31 and an actuating rod 32 is held in the boring 25 by means of a screw 33. The spherical face end 34 of the rod 32 is slightly pressed against a plane face 35 of the block 18. The axis 36 of the vibrator 30 is parallel to the cutting edge 2. The spring 20 may be slightly bent towards the vibrator 30 in the unloaded state before the vibrator 30 is mounted in position such that with the deflection of the spring 20 required for the preload force of the block 18 against the rod 32 the spring 20 gets plain and vertical. The axis 36 passes through the center of gravity 40 of the block 18.

The vibrator 30 is connected to an oscillator 37 by means of a cable 38. Two adjustment knobs 39 on the oscillator 37 allow the selection of the amplitude and frequency of the oscillation of the vibrator 30. Preferably, the frequency is selected in the ultrasound range above 15 kHz. The required amplitude is then only in the range of 10-1000 nm.

Figure 4:
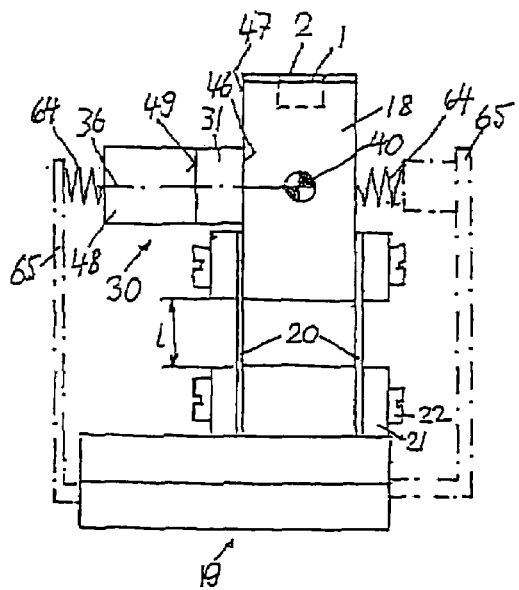
FIG. 4 is a side view of a second embodiment according to the present invention.
Figure 5:
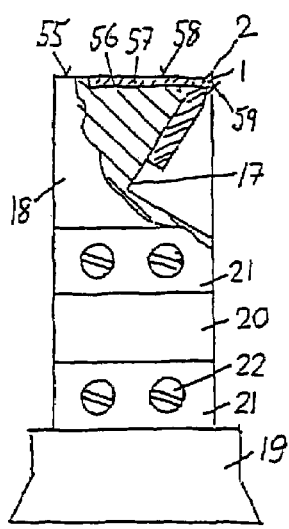
FIG. 5 is a front view, partially in section, of the second embodiment of FIG. 4.

FIGS. 4 and 5 show a second embodiment. Similar parts are designated with the same reference numerals so that a detailed description of those parts is omitted. The embodiment of FIGS. 4 and 5 has two parallel leaf springs 20 of equal active length L. The upper and lower ends of the active length L of the two springs 20 lay in horizontal planes which are parallel to the cutting edge 2. This arrangement has the advantages that the cutting edge 2 moves more parallel to itself than in the first embodiment. In the first embodiment it makes a minute pendulum motion, and that vibrations around a vertical axis are strongly restricted.

In this embodiment the piezoelectric thickness transducer 31 is directly attached, e.g., bonded with one of its plane end faces 46 to a vertical face 47 of the block 18. A counter mass 48 is fastened to the opposite end face 49 of the transducer. Instead of or in addition to directly bonding the faces 46 and 49 to the block 18 and counter mass 48, a pressing force by springs 64 may be used which may bear against arms 65 attached to the holder 19. This variant is shown in dash-dotted lines in FIG. 4.

This arrangement of the vibrator 30 has the advantage that considerably higher accelerations of the block 18 towards the counter mass 48 are possible. This is particularly of advantage when higher frequencies are used, e.g., in the ultrasound range because the accelerations increase with the square of the frequency.

The embodiment of FIG. 5 is shown in the variant for dry ultramicrotomy, e.g., without the water 5 in a trough behind the blade 1. Instead, the upper, horizontal face 55 of the block 18 has a depression 56 which is filled with a plastic insert 57 with a plane upper surface 58, the plane of which intersecting the front face 59 of the blade 1 at an angle of 75° to 85°, preferably about 80°. Therefore, when the blade 1 is set at the recommended clearance angle of 10°, the surface 58 is exactly horizontal which greatly facilitates observation of the cut sections 4 with a stereo microscope, e.g., for section pick-up since no refocusing is required when moving the microscope horizontally. A material with good triboelectrical properties for the insert 57 is an epoxy resin.

Instead of the piezoelectric transducer 31, other types of transducers could be used, e.g., magnetic transducers. A suitable transducer would be a moving coil transducer similar to the one used in moving coil loudspeakers. The moving coil would be mounted to the block 18 and connected to the oscillator 37. The (e.g., permanent) magnet surrounding the coil and acting as counterweight could be elastically suspended (e.g., like the block 18 in FIG. 4) on the holder 19. The axis of the coil would be coincident with the axis 36.

Figure 6:
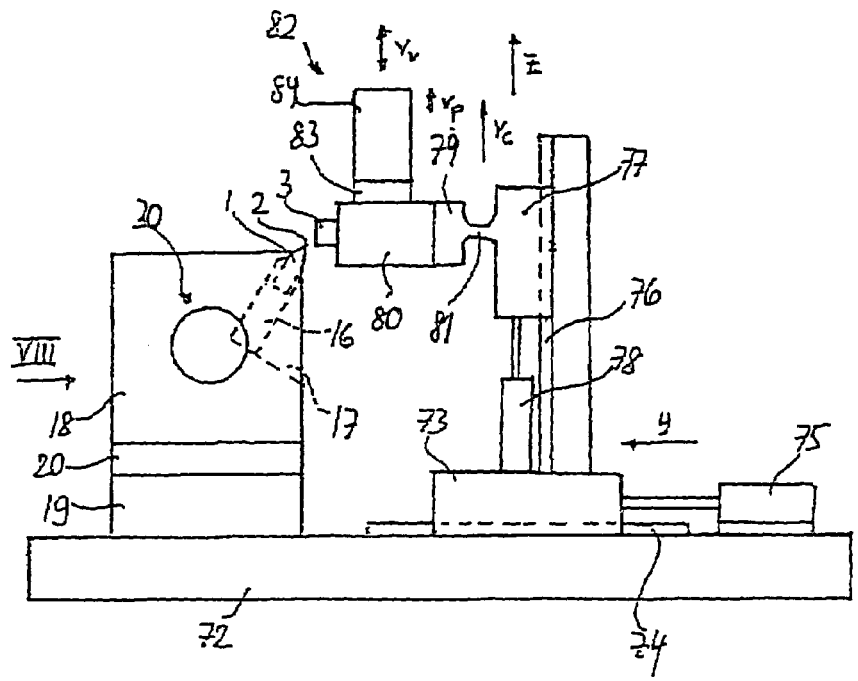
FIG. 6 is a side view of a third embodiment according to the present invention.
Figure 7:
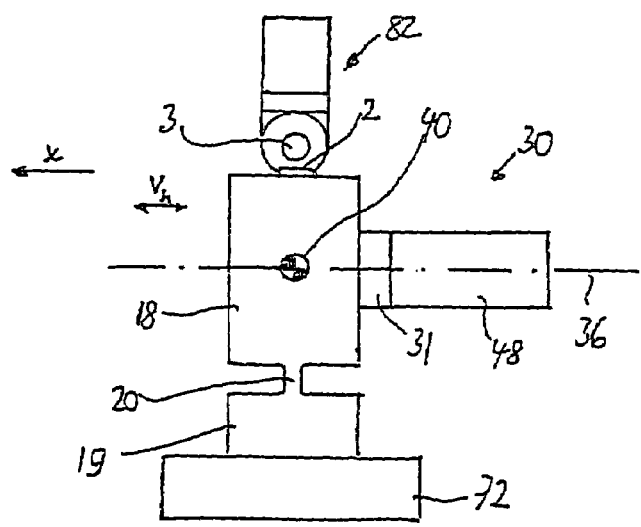
FIG. 7 is a front view of the third embodiment of FIG. 6.
Figure 8:
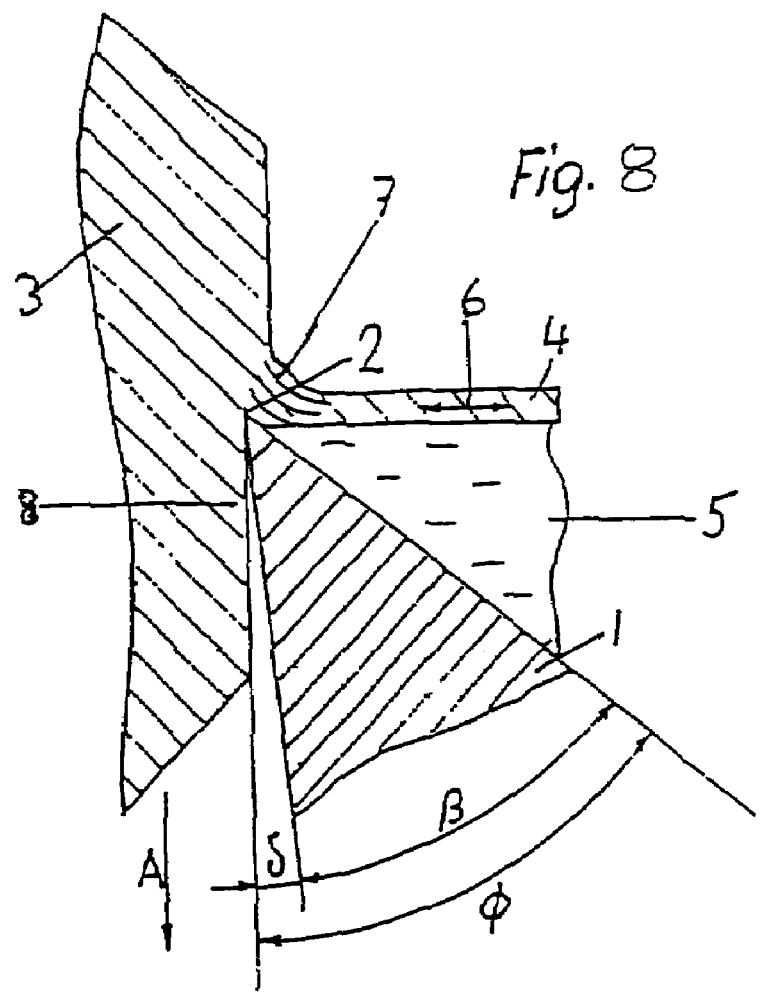
FIG. 8 is a schematic diagram depicting the cutting action of a blade or knife according to the prior art.

FIGS. 6 and 7 show a third embodiment. Similar parts are again designated with the same reference numerals. In this embodiment, the holder 19, the block 18 and the leaf spring 20 are manufactured from a single piece of metal. The spring 20 is a web connecting the holder 19 and the block 18. The holder 19 is mounted on a base 72. In operation, the block 18 oscillates with an amplitude $a_o$ and with a frequency in radians $\omega=2\pi\cdot\nu$, wherein $\nu$ is the frequency in Hz, in a horizontal first direction x parallel to the cutting edge 2. The oscillating movement is $a_o \sin \omega t$ and the oscillating speed $v_h$ is $a_o \omega \cos \omega t$.

A first slide 73 is slidably guided on first guide rails 74 of the base 72 which extend in a horizontal second direction y perpendicular to the first direction x. The movement of the slide 73 is controlled by a first actuator 75 for stepwise advance of the probe 3 towards the cutting edge 2 between successive cuts. Second guide rails 76 are mounted on the slide 73 and extend in the vertical direction z which is perpendicular to the first direction x and the second direction y. A second slide 77 is slidably guided in the rails 76. The movement of the second slide 77 is controlled by a second actuator 78 which controls the vertical cutting speed $v_c$ of the probe 3 relative to the cutting edge 2.

A base 79 of a chuck 80 is mounted to the slide 77 by means of a second leaf spring 81. The base 79, spring 81 and slide 77 are again shown as manufactured from a single metal block. The plane of the spring 81 is horizontal, i.e., parallel to the cutting edge 2 and perpendicular to the plane of the spring 20. The chuck 80 clamps the probe or sample 3. A second vibrator 82 is mounted on the chuck 80. It consists of a piezoelectric transducer 83, which is bonded with one face end to the chuck 80, and a counter mass 84 which is bonded to the opposite face end of the transducer 83.

In operation, the chuck 80 and therewith the probe 3 is advanced vertically by the actuator 78 with a constant cutting speed $v_c$ for cutting. A vertical oscillation by the vibrator 82 is superimposed on the cutting speed $v_c$ with an amplitude $b_o$ and a frequency $2\omega$ which is twice the oscillating frequency of the vibrator 30. The oscillating movement is $b_o \cos(2\omega t - \pi/2)$ and the oscillating speed $v_v$ is $-2b_o \omega \sin(2\omega t - \pi/2)$. The total vertical speed $v_p$ of the probe is therefore $$v_p = v_c + v_v = v_c - 2 b_o \omega \sin(2\omega t - \pi/2)$$

The vertical amplitude $b_o$ and the frequency $\omega$ are now chosen such that $$2 b_o \omega \geq v_c$$

In this way the actual vertical cutting speed $v_p$ of the probe is zero or negative when the horizontal speed $v_h$ is zero, i.e., when $\omega t = \pi/2 + n \cdot \pi$ where n is an integer number.

In other words, the phase angle, the amplitude $b_o$ of the vertical oscillation and the frequency $\omega$ are chosen such that the actual vertical speed $v_p$ of the probe is zero or negative when the horizontal movement of the knife 1 reaches its reversal points.

It is also possible to vibrate the probe in a horizontal direction, i.e., at least approximately parallel to the cutting edge of the blade. Preferably, the probe and the blade are vibrated such that when the blade 1 reaches its reversal points, the probe is still moving, preferably at maximum speed and vice versa. Preferably, the probe and the blade are vibrated at the same frequency, but not in the same phase.

By vibrating the probe either in a vertical or a horizontal direction, section compression can be completely avoided even in these reversal points.

As an example for the vibration in a vertical direction: when the horizontal frequency $\omega$ is $2\pi \cdot 16\,\text{kHz} = 10^5\,\text{s}^{-1}$ and the advance speed $v_c = 2\,\text{mm}\cdot\text{s}^{-1}$ then the vertical amplitude $b_o$ would have to be at least 10 nm. The horizontal amplitude $a_o$ is again considerably less than 1 μm. In the above example, with the requirement that $\tan \alpha \leq 0.1$ the horizontal amplitude $a_o$ of the knife 1 would have to be at least 200 nm ($a_o \omega \leq 20$ mm/s). With lower cutting speeds $v_c$, the amplitudes $a_o$ and $b_o$ can be reduced accordingly.

Of course, the relative movement between the knife 1 and the probe 3 can be achieved in different ways than the one specifically shown in FIG. 6., e.g., the slide 73 and/or the slide 77 could be associated with the holder 19 instead of with the chuck 80, or the horizontal and vertical vibrations could be reversed, i.e., that the knife 1 oscillates vertically and the chuck 80 horizontally, or both vibrations could be imparted on the same elements, knife 1 or chuck 80.

The invention claimed is:

1. A process for cutting sections from a probe for microscopic analysis, by using an ultramicrotome device having a blade with a cutting edge, the cutting edge in a non-vibrated position extending at least approximately in a first direction, the process comprising the steps of:
   vibrating the blade in the first direction;
   vibrating the probe;
   between successive cuts, effecting relative movement between the probe and the blade in a second direction in a stepwise manner, the second direction being perpendicular to the first direction; and
   during each cut, effecting relative movement between the probe and the blade in a third direction perpendicular to the first and second directions, whereby the probe is cut in sections
   wherein the probe is vibrated approximately parallel to the first direction, and
   wherein the probe and blade are vibrated such that when the blade reaches its reversal points, the probe is still moving and vice versa.

2. The process according to claim 1, wherein the probe is cut in sections having a thickness of about 10 to about 100 nm.

3. The process according to claim 1, wherein the blade is vibrated with a maximum amplitude of about 1 μm.

4. The process according to claim 1, wherein the ultramicrotome device includes a block holding the blade, wherein the process further comprises the step of applying force to the block.

5. The process according to claim 1, wherein the probe is vibrated in the third direction.

6. The process according to claim 5, wherein the blade is vibrated in a first frequency and the probe is vibrated in a second frequency, the second frequency being about twice the first frequency.

7. The process according to claim 5, wherein the probe is vibrated with an amplitude $b_o$ of vibration with $$b_o \geq v_c/2\omega,$$

wherein $\omega$ is the frequency in radians per second of the vibration of the blade and $v_c$ is the cutting speed in the third direction.

8. The process according to claim 1, wherein the blade is vibrated in the first direction with a frequency above about 15 kHz.

9. The process according to claim 1, wherein the probe and the blade are vibrated at the same frequency, but in a different phase.

10. The process according to claim 1, wherein, during each cut, relative movement between the vibrating probe and the vibrating blade in the third direction is effected with a substantially constant cutting speed over a distance larger than a cross-sectional dimension of the probe in the third direction.

11. The process according to claim 1, wherein during each cut, relative movement between the vibrating probe and the vibrating blade in the third direction is effected with a substantially constant cutting speed.

12. The process according to claim 1, wherein the blade is vibrated with an amplitude $a_o$ of vibration with $$a_o \geq 10\, v_c/\omega,$$

wherein $\omega$ is the frequency in radians per second of the vibration of the blade and $v_c$ is the cutting speed in the third direction.

13. The process according to claim 1, wherein a diamond blade is used.

* * * * *